United States Patent
Oka

(10) Patent No.: US 11,172,808 B2
(45) Date of Patent: Nov. 16, 2021

(54) ENDOSCOPE

(71) Applicant: OLYMPUS CORPORATION, Hachioji (JP)

(72) Inventor: Tetsuhiro Oka, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 176 days.

(21) Appl. No.: 16/535,138

(22) Filed: Aug. 8, 2019

(65) Prior Publication Data
US 2019/0357755 A1 Nov. 28, 2019

Related U.S. Application Data

(63) Continuation of application No. PCT/JP2017/006949, filed on Feb. 23, 2017.

(51) Int. Cl.
*A61B 1/00* (2006.01)
*A61B 1/05* (2006.01)
*A61B 1/07* (2006.01)

(52) U.S. Cl.
CPC ............ *A61B 1/00177* (2013.01); *A61B 1/05* (2013.01); *A61B 1/07* (2013.01)

(58) Field of Classification Search
CPC combination set(s) only.
See application file for complete search history.

(56) References Cited

U.S. PATENT DOCUMENTS

| | | | |
|---|---|---|---|
| 4,483,585 A * | 11/1984 | Takami | A61B 1/07 385/115 |
| 2005/0018431 A1 | 1/2005 | Shiang | |
| 2014/0347878 A1* | 11/2014 | Honda | A61B 1/00177 362/574 |

(Continued)

FOREIGN PATENT DOCUMENTS

| | | | |
|---|---|---|---|
| CN | 1823433 A | 8/2006 | |
| CN | 100530751 C | 8/2009 | |
| EP | 2815691 A1 | 12/2014 | |
| JP | H08254658 A | 10/1996 | |
| JP | 2013161645 A | 8/2013 | |
| JP | 2014087482 A * | 5/2014 | ........... A61B 1/0615 |
| JP | 5596889 B1 | 8/2014 | |

(Continued)

OTHER PUBLICATIONS

International Search Report (ISR) (and English language translation thereof) dated May 16, 2017 issued in International Application No. PCT/JP2017/006949.

*Primary Examiner* — Timothy J Neal
(74) *Attorney, Agent, or Firm* — Holtz, Holtz & Volek PC

(57) ABSTRACT

An endoscope according to the present invention includes an insertion section, a forward observation window and a forward illumination system disposed at a distal end surface of the insertion section, a lateral observation window and a lateral illumination system disposed toward a proximal end, and an image capturing element captures an image of light. The forward illumination system includes a scattering element surrounding the forward observation window, and light guide fibers that cause illumination light from a light source to enter, toward a distal end, input locations arranged in a circumferential direction at a proximal end of the scattering element. The scattering element is constituted by dispersing particles in a homogenous medium, and satisfies the conditional expressions $0.06 \leq \mu s \leq 100$ and $0.7 \leq g < 1$, where $\mu s$ indicates a scattering coefficient (1/mm) of the scattering element and g indicates an anisotropy parameter of the particles.

7 Claims, 11 Drawing Sheets

(56) References Cited

U.S. PATENT DOCUMENTS

| | | |
|---|---|---|
| 2016/0100750 A1 | 4/2016 | Furuta |
| 2017/0215714 A1 | 8/2017 | Shinji et al. |
| 2017/0269348 A1 | 9/2017 | Shinji |

FOREIGN PATENT DOCUMENTS

| | | | |
|---|---|---|---|
| JP | 2015016020 A | 1/2015 | |
| WO | 2005018010 A2 | 2/2005 | |
| WO | WO-2014115639 A1 * | 7/2014 | ............ C09J 133/00 |
| WO | 2015005108 A1 | 1/2015 | |
| WO | 2016088267 A1 | 6/2016 | |
| WO | 2016098203 A1 | 6/2016 | |

* cited by examiner

ENDOSCOPE

CROSS-REFERENCE TO RELATED APPLICATIONS

This is a continuation of International Application PCT/JP2017/006949, with an international filing date of Feb. 23, 2017, which is hereby incorporated by reference herein in its entirety.

TECHNICAL FIELD

The present invention relates to endoscopes.

BACKGROUND ART

A known endoscope in the related art can be used for observing forward and laterally, including diagonally rearward, in the insertion direction for, for example, colon observation (e.g. see Publication of Japanese Patent No. 5596889).

This endoscope has a forward observation window and a lateral observation window, which are provided so as to be separate from each other, and also has a forward illumination system and a lateral illumination system. The forward illumination system includes a ring-shaped scattering element surrounding the forward observation window disposed at the distal end surface of an insertion section of the endoscope. An output end of a single optical fiber bundle is disposed at a side surface of the scattering element. Light entering the side surface of the scattering element from the output end is uniformly emitted in accordance with a strong scattering effect of the scattering element.

SUMMARY OF INVENTION

An aspect of the present invention provides an endoscope including: an insertion section having narrow shape; a forward observation window and a forward illumination system that are disposed at a distal end surface of the insertion section; a lateral observation window and a lateral illumination system that are disposed toward a proximal end relative to the distal end surface; and an image capturing element that captures an image of light entering via the forward observation window and the lateral observation window. The forward illumination system includes a ring-shaped scattering element disposed at a position surrounding the forward observation window, and a plurality of light guide fibers that cause illumination light guided from a light source to enter, toward a distal end, a plurality of input locations arranged at intervals in a circumferential direction at a proximal end of the scattering element. The scattering element is constituted by dispersing one or more kinds of particles in a homogenous medium composed of a material different from the particles, and satisfies conditional expressions indicated below:

0.06≤μs≤100

0.7≤g<1 where μs indicates a scattering coefficient (1/mm) of the scattering element and g indicates an anisotropy parameter of the particles.

In the above aspect, the plurality of light guide fibers may be disposed such that proximal end surfaces thereof that receive the illumination light from the light source are grouped together and are disposed at positions facing a light emitting section of the light source.

In the above aspect, the light emitting section may be an output end of an optical fiber bundle that optically guides light from the light source in a longitudinal direction of the insertion section.

In the above aspect, the lateral observation window may be provided in a range between 200° and 300° inclusive in the circumferential direction, and the light guide fibers may be disposed to longitudinally extend across a position of the lateral observation window at a circumferential position where the lateral observation window is not provided.

In the above aspect, the light guide fibers may include three or four light guide fibers and may cause the illumination light to enter the input locations arranged at substantially equal intervals in the circumferential direction.

In the above aspect, the light guide fibers may be plastic multicore fibers.

In the above aspect, a central axis at a distal end of each light guide fiber may be disposed radially outward of the scattering element at an angle ranging between 0° and 30° inclusive relative to an axis orthogonal to the forward observation window from the proximal end toward the distal end.

DESCRIPTION OF EMBODIMENTS

An endoscope 1 according to an embodiment of the present invention will be described below with reference to the drawings.

Figure 1:
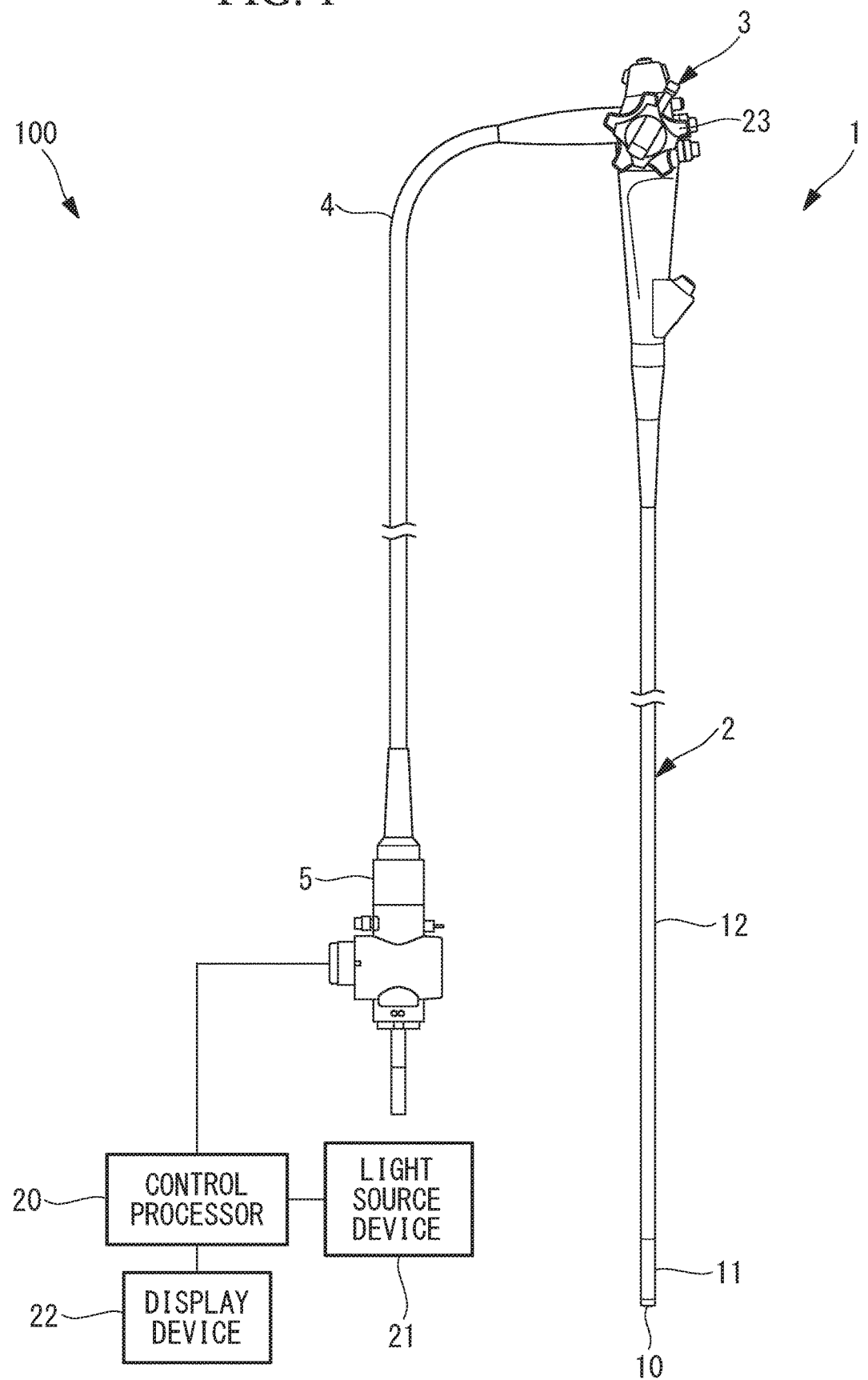
FIG. 1 illustrates the overall configuration of an endoscope according to an embodiment of the present invention.

As shown in FIG. 1, the endoscope 1 according to this embodiment includes a narrow insertion section 2 to be inserted into, for example, a body cavity, an operable section 3 provided at the proximal end of the insertion section 2, a universal cord 4 extending from the operable section 3, and a connector 5 provided at the terminal end of the universal cord 4.

Figure 2:
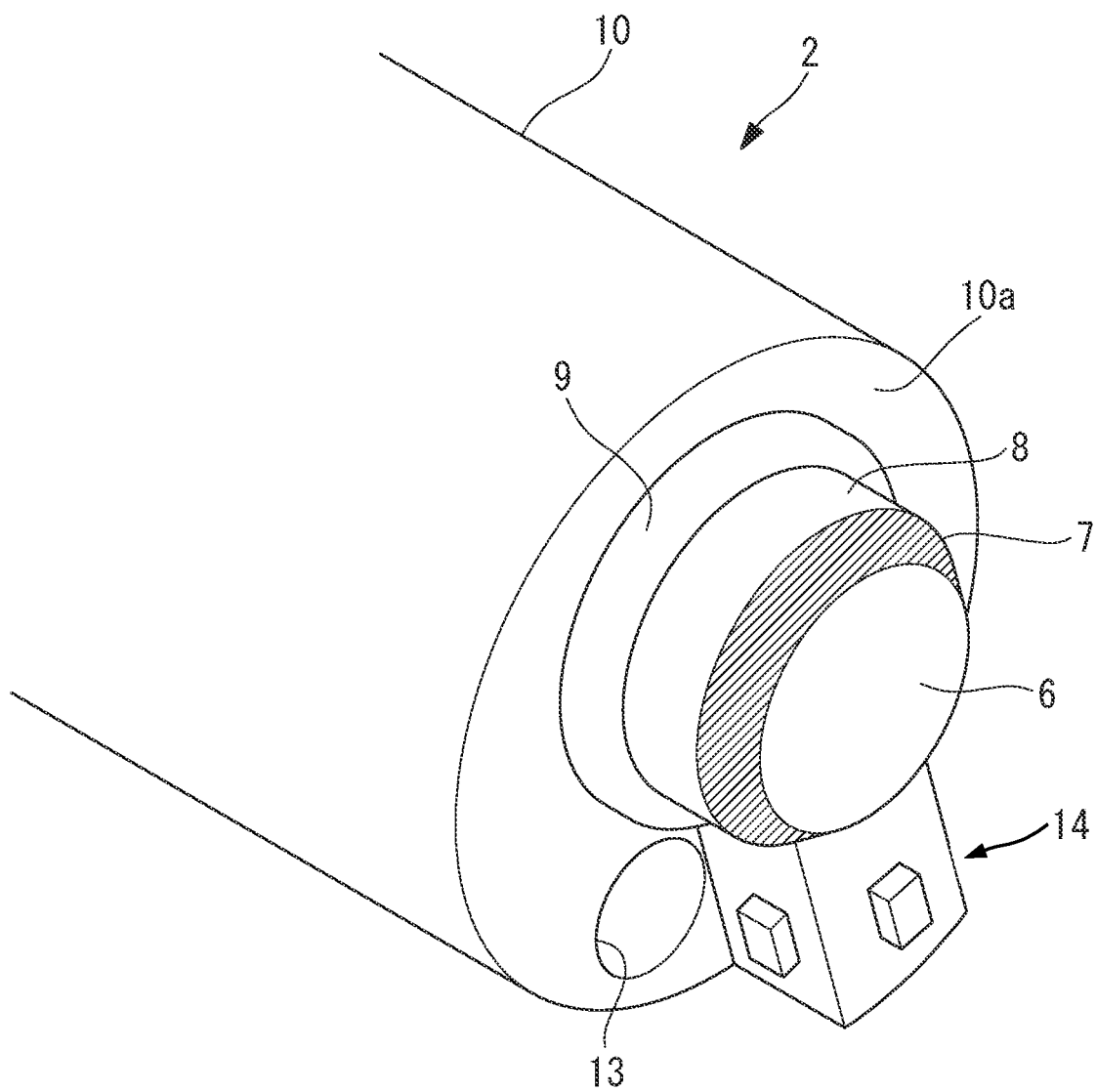
FIG. 2 is an enlarged perspective view illustrating a part of a distal end segment of an insertion section of the endoscope in FIG. 1.
Figure 3:
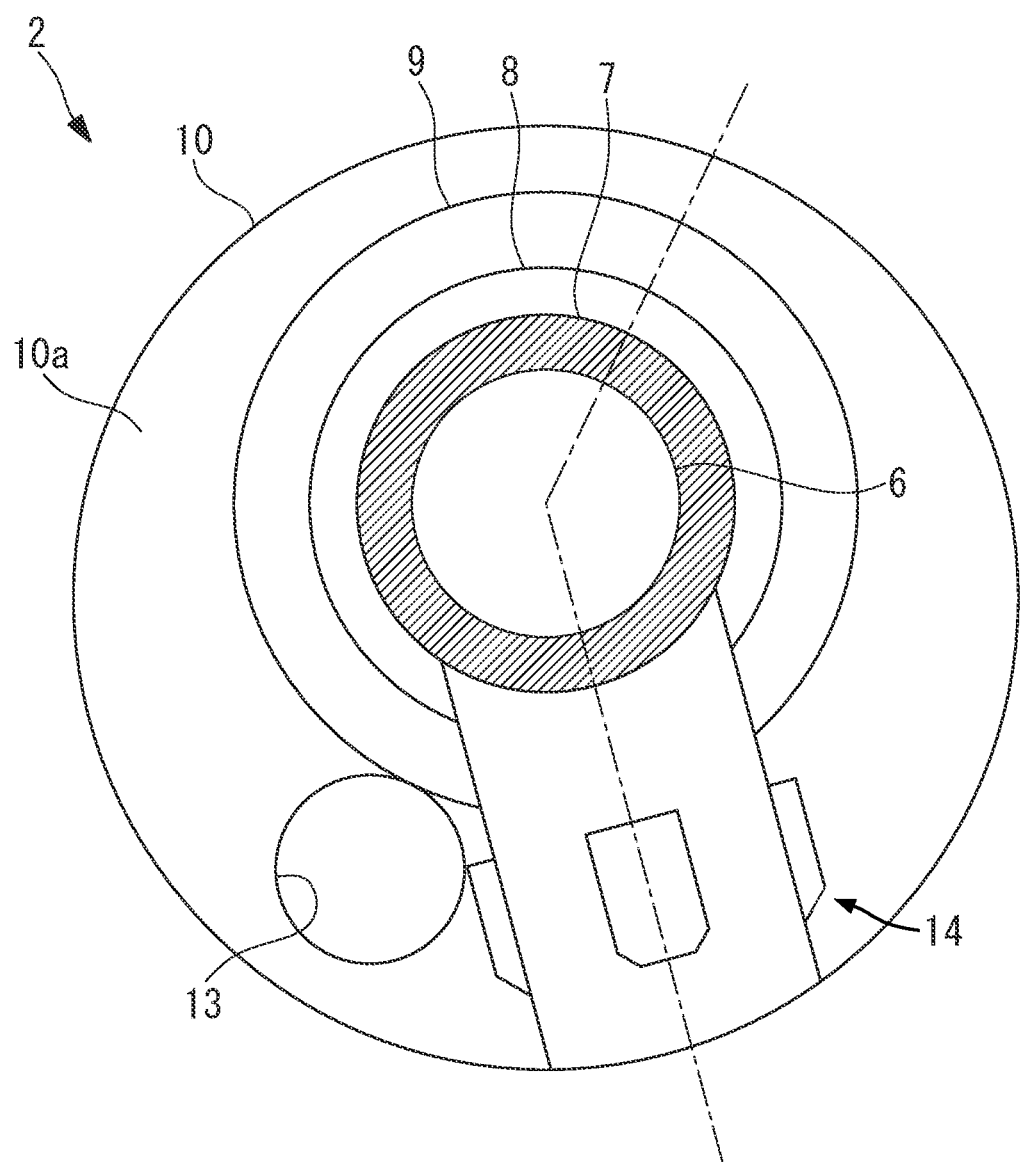
FIG. 3 is a front view illustrating the distal end segment of the insertion section of the endoscope in FIG. 1.
Figure 4:
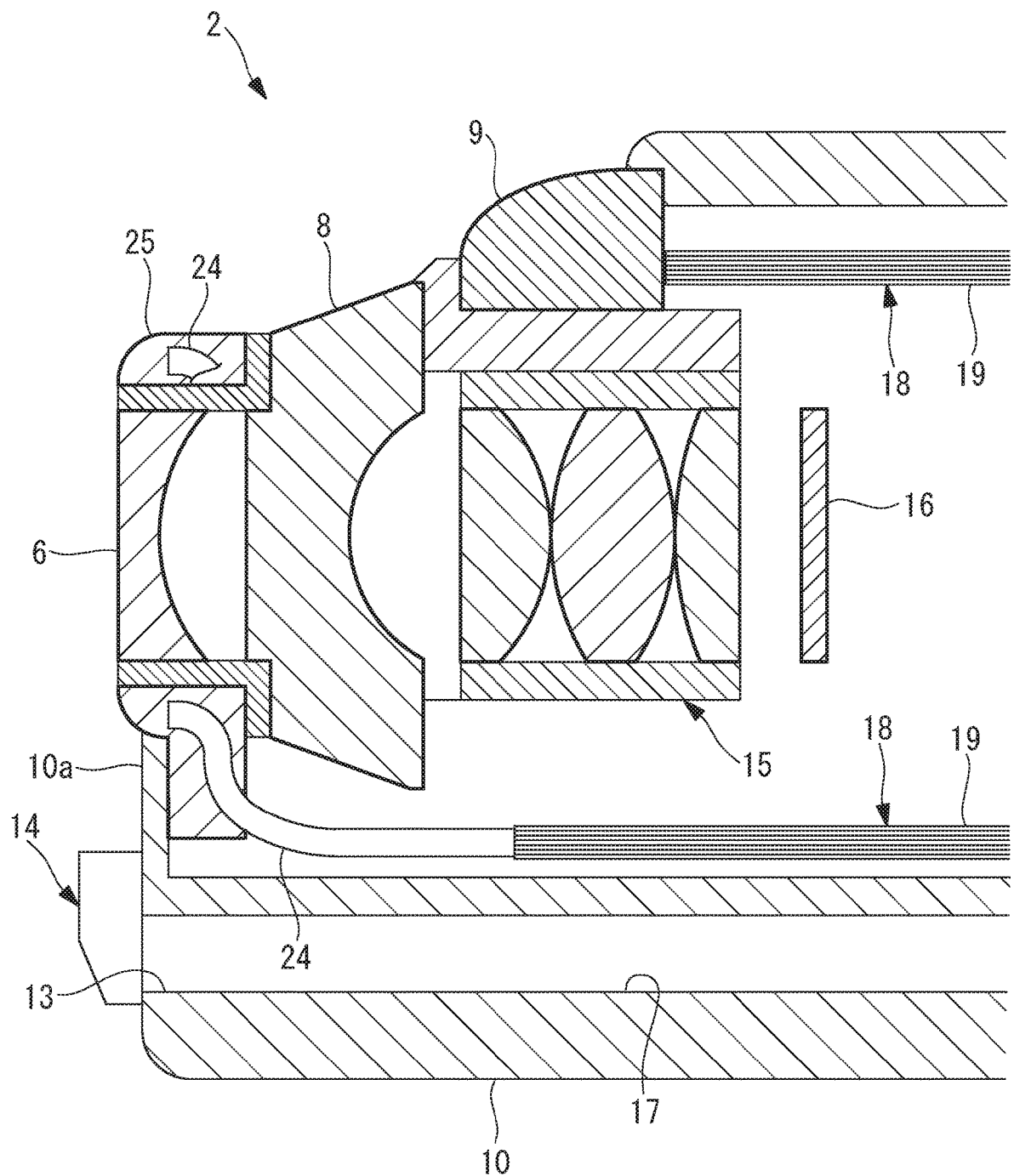
FIG. 4 is a partial vertical sectional view illustrating the distal end segment of the insertion section of the endoscope in FIG. 1.

As shown in FIGS. 2 to 4, at the distal end of the insertion section 2, a direct-vision forward-observation objective lens (forward observation window) 6 is disposed facing forward on a distal end surface 10a, and a ring-shaped forward illumination system 7 for forward illumination is disposed surrounding the forward-observation objective lens 6. A lateral-vision lateral-observation objective lens (lateral observation window) 8 and an illumination lens (lateral illumination system) 9 are disposed toward the proximal end of the insertion section 2 relative to the forward illumination system 7. Accordingly, the endoscope 1 according to this embodiment has a wide visual field that allows for simultaneous observation of the forward visual field and the lateral visual field.

The forward-observation objective lens 6 forms an image of a subject located in front of the insertion section 2. The lateral-observation objective lens 8 has the shape of a circular truncated cone that tapers forward so as to form an image of a subject located lateral to the insertion section 2.

As shown in FIG. 1, the insertion section 2 includes a rigid distal end segment 10 provided at the most distal end, a bending segment 11 that connects to the proximal end of the distal end segment 10, and a flexible tubular segment 12 that connects to the proximal end of the bending segment 11 and that is formed of a long tubular member having flexibility. The distal end segment 10 has an outer diameter of 14 mm or smaller.

As shown in FIGS. 2 and 3, for example, a surgical-device channel opening 13, the forward-observation objective lens 6, the illumination lens 9, and a water nozzle 14 are disposed at the distal end of the distal end segment 10.

As shown in FIG. 4, an imaging optical system 15 that forms an image of light focused by the forward-observation objective lens 6 and the lateral-observation objective lens 8 and an image capturing element 16 that captures the image of the subject, which is formed by the imaging optical system 15, are provided within the distal end segment 10 of the insertion section 2.

A surgical-device channel 17, a light guide (optical fiber bundle) 18, and a signal cable (not shown), for example, are disposed within the insertion section 2. The surgical-device channel 17 extends in the longitudinal direction through the insertion section 2 from the surgical-device channel opening 13 to a surgical-device insertion opening disposed near the connection between the insertion section 2 and the operable section 3. The light guide 18 and the signal cable extend in the longitudinal direction through the insertion section 2 from the distal end segment 10 of the insertion section 2, extend through the operable section 3 and through the universal cord 4, and ultimately connect to the connector 5 at the terminal end of the universal cord 4.

The light guide 18 is constituted of a fiber bundle formed by binding together a plurality of light guide fibers 19 for optically guiding illumination light.

An endoscope system 100 is constituted by connecting a control processor 20, a light source device (light source) 21, and a display device 22, which are external devices, to the endoscope 1 by means of the connector 5.

The operable section 3 is a part to be held by a user when using the endoscope 1. A bending knob 23 and a plurality of operable members corresponding to various kinds of movements are disposed on the outer surface of the operable section 3. For example, the bending knob 23 is an operable member for bending the bending segment 11 of the insertion section 2 in any of the upward, downward, leftward, and rightward directions by being manually rotated by the user.

The light source device 21 generates illumination light. The control processor 20 is a signal processor that comprehensively controls the entire endoscope system 100. The display device 22 displays an endoscopic image based on an image signal acquired by the endoscope 1 and is formed of, for example, an LCD panel.

The control processor 20 performs transmission of control signals, various types of detection signals, and acquired image signals via the signal cable extending through the endoscope 1. Then, processed image signals are transmitted to the display device 22 where endoscopic images and various kinds of information are displayed. The illumination light from the light source device 21 is guided to the illumination lens 9 disposed in the insertion section 2 via the connector 5, the universal cord 4, and the operable section 3, so as to be radiated onto a surrounding observation target.

Figure 5:
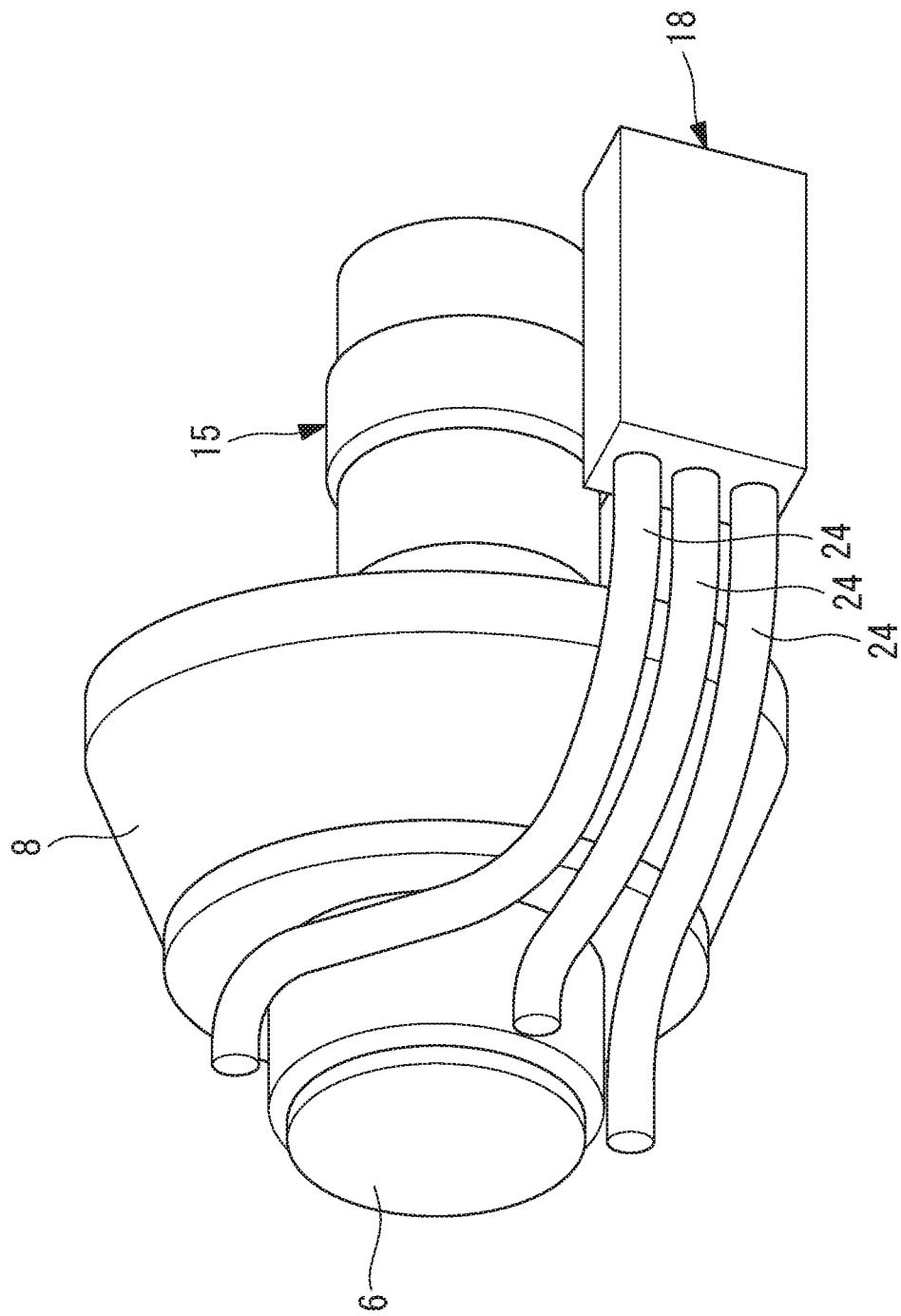
FIG. 5 is a perspective view illustrating the internal structure of the distal end segment of the insertion section of the endoscope in FIG. 1.

As shown in FIGS. 4 and 5, the forward illumination system 7 includes light guide fibers 24 that receive the illumination light optically guided through the insertion section 2 by the light guide 18, and also includes a ring-shaped scattering element 25 that scatters the illumination light optically guided by the light guide fibers 24.

In this embodiment, three light guide fibers 24 are provided. Each light guide fiber 24 is formed of a plastic multicore fiber.

Each light guide fiber 24 formed of a plastic multicore fiber preferably has, for example, an outer diameter ranging from 0.2 mm to 1 mm and a numerical aperture ranging from 0.2 to 0.7, and is constituted by binding together a plurality of cores, for example, 200 or more cores, composed of polymethylmethacrylate (PMMA) resin. Each core has a diameter of 100 μm or smaller, preferably 50 μm or smaller, and more preferably about 30 μm. The cladding of the multicore fiber is composed of fluorine resin.

Figure 6:
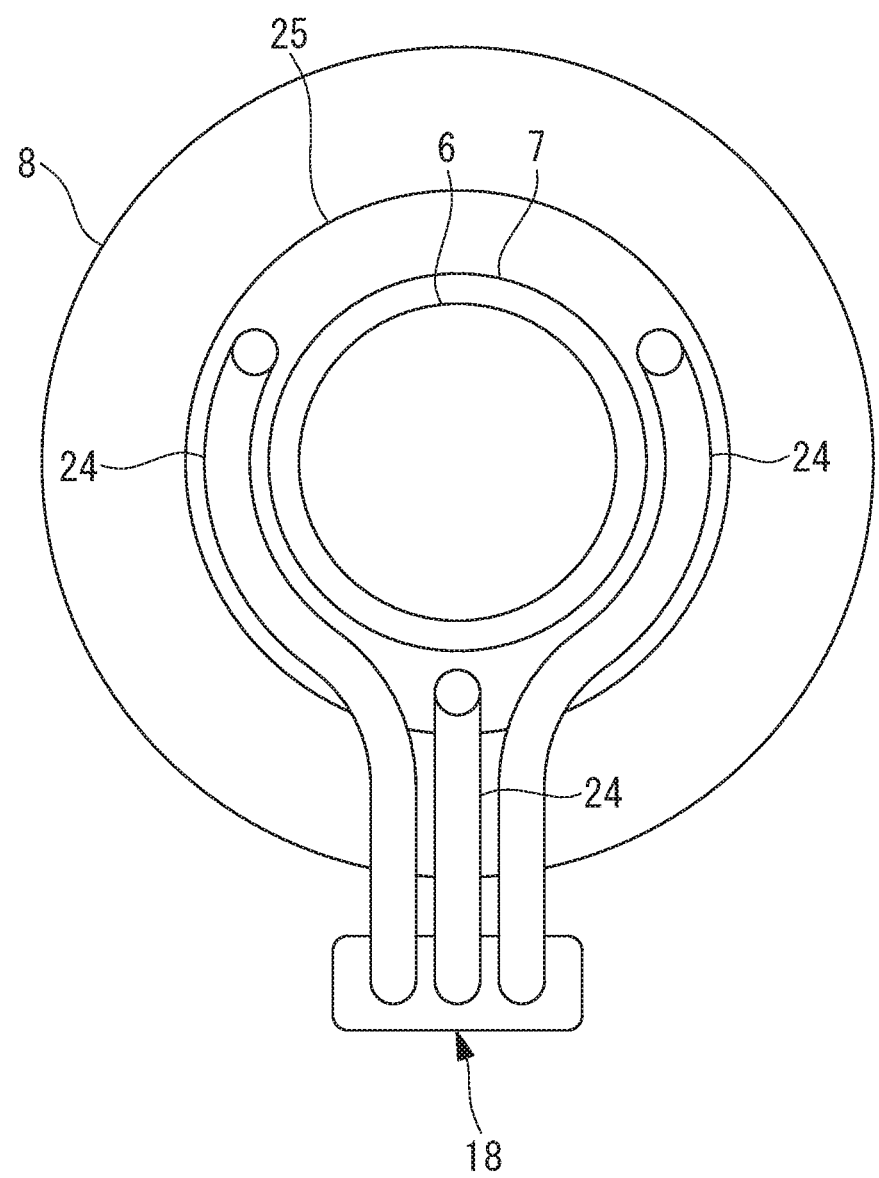
FIG. 6 is a front view illustrating the arrangement of light guide fibers of the endoscope in FIG. 1.

The distal end of each light guide fiber 24 is disposed facing an input location at the proximal end surface of the scattering element 25 such that the illumination light is caused to enter the ring-shaped scattering element 25 from the proximal end surface toward the distal end surface of the scattering element 25. As shown in FIG. 6, the three input locations that receive the illumination light from the three light guide fibers 24 are arranged at equal intervals in the circumferential direction.

Figure 10:
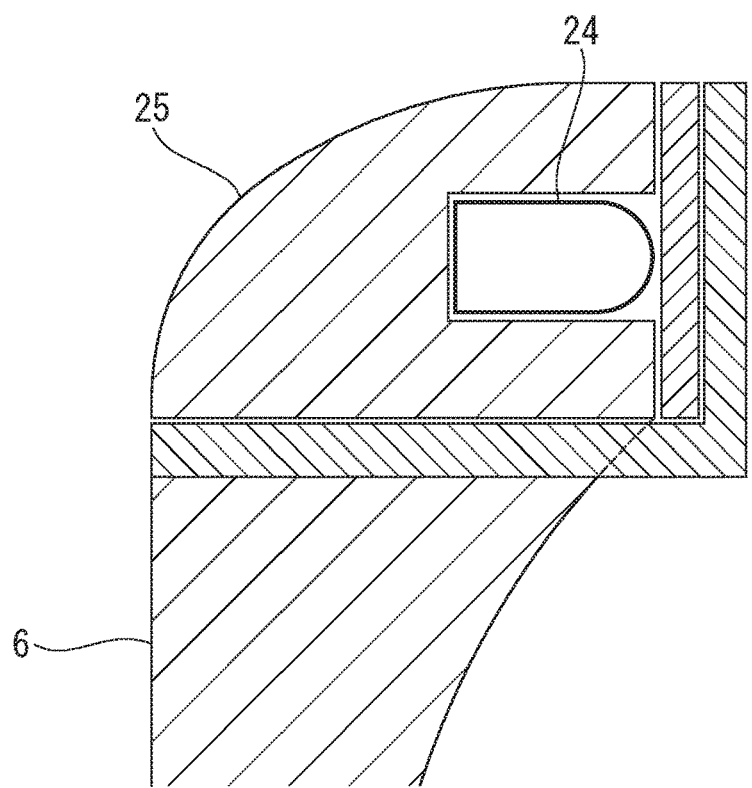
FIG. 10 is a partial vertical sectional view illustrating the direction of the distal end of each light guide fiber relative to the scattering element in the endoscope in FIG. 1.

As shown in FIGS. 5 and 10, the distal end surface and the proximal end surface of each light guide fiber 24 are disposed substantially parallel to the distal end surface of the forward-observation objective lens 6. The proximal end surface of each light guide fiber 24 is disposed toward the proximal end relative to the lateral-observation objective lens 8.

The proximal ends of the three light guide fibers 24 are grouped together in one area. The proximal end surface of each light guide fiber 24 is disposed facing the distal end surface (light emitting section) of the light guide 18. Thus, the illumination light optically guided by the light guide 18 is input to the proximal end surfaces of the light guide fibers 24 and is output from the distal end surfaces of the light guide fibers 24, so that the illumination light can be caused to enter the scattering element 25. The proximal end surfaces of the light guide fibers 24 and the distal end surface of the light guide 18 are adhered to each other by a transparent adhesive, where necessary.

Specifically, the light guide fibers 24 extend across, in the longitudinal direction of the insertion section 2, positions of the lateral-observation objective lens 8 in one circumferential area of the lateral-observation objective lens 8 from the proximal side relative to the lateral-observation objective lens 8, then bend twice in the opposite direction, and are disposed such that the distal end surfaces thereof respectively face the three input locations in the scattering element 25. The distal end surfaces of the light guide fibers 24 are adhered to the scattering element 25 at the respective input locations by using a transparent adhesive.

The view angle of the lateral-observation objective lens 8 is set between 200° and 300° inclusive, and the light guide fibers 24 extend past the lateral-observation objective lens 8 in the front-rear direction (i.e., the longitudinal direction) at a position (i.e., a circumferential position) outside the visual field of the lateral-observation objective lens 8.

The scattering element 25 is disposed at a position surrounding the forward-observation objective lens 6 and is composed of an optically transparent resin material (i.e., a homogenous medium or resin) having at least one kind of particles dispersed therein. The particles cause the illumination light to scatter in accordance with Mie scattering.

With regard to the scattering element 25, a scattering coefficient $\mu s$ (1/mm) and an anisotropy parameter g in the Mie scattering theory satisfy the following conditional expressions.

$$0.06 \leq \mu s \leq 100 \quad (1)$$

$$0.7 \leq g < 1 \quad (2)$$

When these conditional expressions are satisfied, the scattering properties of the scattering element 25 are sufficiently low, the illumination light can be gradually expanded by scattering, back-scattering can be reduced, and a component of the illumination light returning toward the light guide 18 can be sufficiently reduced.

The particles used may be inorganic particles composed of, for example, silica, alumina, talc, zirconia, a zinc oxide, or a titanium dioxide, or organic particles composed of, for example, polymethylmethacrylate resin, polystyrene resin, polyurethane resin, benzoguanamine resin, or silicone resin. Alternatively, air bubbles may be used as the particles.

The resin material used may be, for example, polyester resin, acrylic resin, acrylic urethane resin, polyester acrylate resin, polyurethane acrylate resin, epoxy acrylate resin, urethane resin, epoxy resin, polycarbonate resin, cellulose resin, acetal resin, vinyl resin, polyethylene resin, polystyrene resin, polypropylene resin, polyamide resin, melamine resin, phenol resin, silicone resin, or fluorine resin. If the resin material is to be used as an outermost layer of the endoscope 1 to be inserted into the human body, it is desirable that cycloolefin resin or sulfonate resin be used from the standpoint of, for example, biocompatibility and chemical resistance.

If the conditions (1) and (2) are satisfied, the light guide fibers 24 disposed facing the input locations are visually recognizable when the scattering element 25 is viewed from the distal end (i.e., the output surface). Although the light guide fibers 24 are directly viewable if the scattering properties are low, the light guide fibers 24 are still recognizable even when the scattering properties are high by introducing illumination light.

Figure 7:
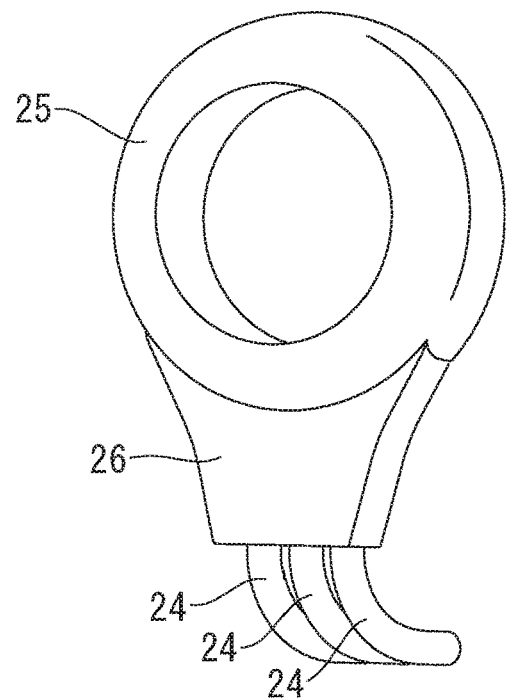
FIG. 7 is a perspective view illustrating an assembly of a scattering element and the light guide fibers of the endoscope in FIG. 1.
Figure 8:
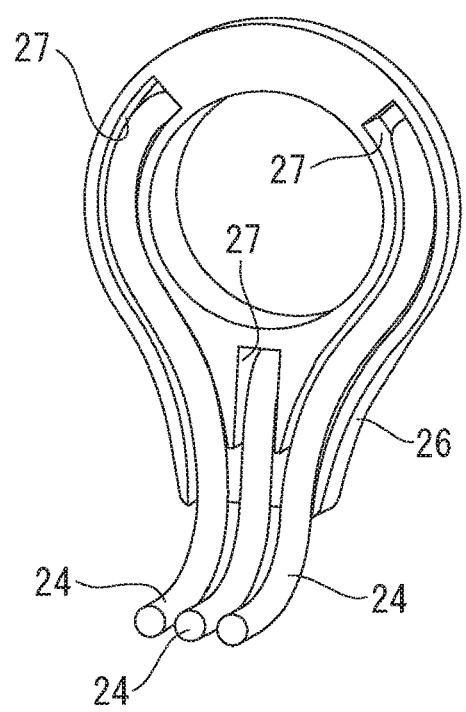
FIG. 8 is a perspective view of the assembly in FIG. 7, as viewed from the proximal end thereof.
Figure 9:
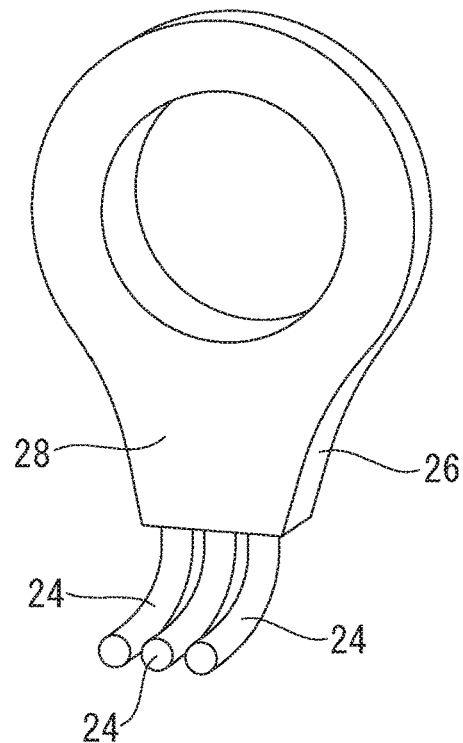
FIG. 9 is a perspective view illustrating a state where a cover is attached to the proximal end of the assembly in FIG. 9.

As shown in FIGS. 7 to 9, the scattering element 25 is provided with a support portion 26 extending radially outward from the ring-shaped portion. As shown in FIG. 8, the support portion 26 has grooves 27 for accommodating the three light guide fibers 24 therein. The light guide fibers 24 are accommodated and adhered to the grooves 27 in a one-to-one fashion, so that the support portion 26 supports the light guide fibers 24 in a state where they are fixed to the scattering element 25.

In this embodiment, the scattering element 25 is disposed along the peripheral edge of the distal end surface 10a of the insertion section 2, so that a rounded surface is formed along the entire circumference, as shown in FIGS. 4 and 7, thereby achieving improved insertability of the insertion section 2 into a body cavity. A single-piece component having no seams between a part that functions as an optical element and a part that supports the light guide fibers 24 is formed such that joints between a plurality of components are not exposed on the outer peripheral surface of the insertion section 2. As shown in FIG. 9, the proximal end surface of the scattering element 25 accommodating the light guide fibers 24 within the grooves 27 is closed by a cover 28.

The illumination lens 9 is disposed at the radially outer side of the imaging optical system 15 so as to surround the imaging optical system 15 over a predetermined circumferential range centered on the optical axis of the imaging optical system 15. The outer diameter of the lateral-observation objective lens 8 is set to be larger than the outer diameter of the scattering element 25, and the outer diameter of the illumination lens 9 is set to be larger than the outer diameter of the lateral-observation objective lens 8.

The operation of the endoscope 1 according to this embodiment having the above-described configuration will be described below.

In the endoscope 1 according to this embodiment, the illumination light optically guided by the light guide 18 is output from the distal end surface of the light guide 18 and enters the proximal end surfaces of the three light guide fibers 24 disposed facing the distal end surface. The illumination light entering the light guide fibers 24 is optically guided by the light guide fibers 24 and enters the ring-shaped scattering element 25 surrounding the forward-observation objective lens 6 at the distal end of the insertion section 2.

Because the three light guide fibers 24 are disposed facing the output surface at the input locations arranged at equal intervals in the circumferential direction of the ring-shaped scattering element 25, the illumination light enters the scattering element 25 at the three circumferential locations in the scattering element 25, is scattered by the particles while being optically guided through the scattering element 25, and is mainly output forward.

In this case, since the scattering element 25 satisfies conditional expressions (1) and (2), the scattering properties thereof are kept low, the illumination light can be gradually expanded by scattering, back-scattering can be reduced, and a component of the illumination light returning toward the light guide 18 can be sufficiently reduced.

As a result, the ring-shaped scattering element 25 does not emit light uniformly. Instead, the input locations of the illumination light from the light guide fibers 24 emit light with high intensity, whereas the remaining areas emit light with lower intensity. Accordingly, the entire scattering element 25 is prevented from becoming a secondary light source, and a ring-shaped patch of light can be prevented from being formed in the image of a subject acquired by the image capturing element 16 even when the subject to be observed is moist biological tissue. In other words, since patches of light in the image are limited only to the input locations of the illumination light at the most, there is an advantage in that the subject can be observed without distraction caused by a ring-shaped patch of light.

In the endoscope 1 according to this embodiment, the scattering properties of the scattering element 25 are kept low, so that back-scattering and a component of the illumination light returning toward the light guide 18 can be sufficiently reduced, thereby increasing the component of the illumination light to be output forward. This is advantageous in that the utilization efficiency of the illumination light can be increased.

In the endoscope 1 according to this embodiment, since the light guide fibers 24 used are formed of plastic multicore fibers, the light guide fibers 24 can be disposed in a bent state with an extremely small curvature radius in the distal end segment 10 of the endoscope 1 having an extremely small, limited installation space, and the illumination light optically guided by the light guide 18 can be distributed to the plurality of input locations in the scattering element 25.

Figure 11:
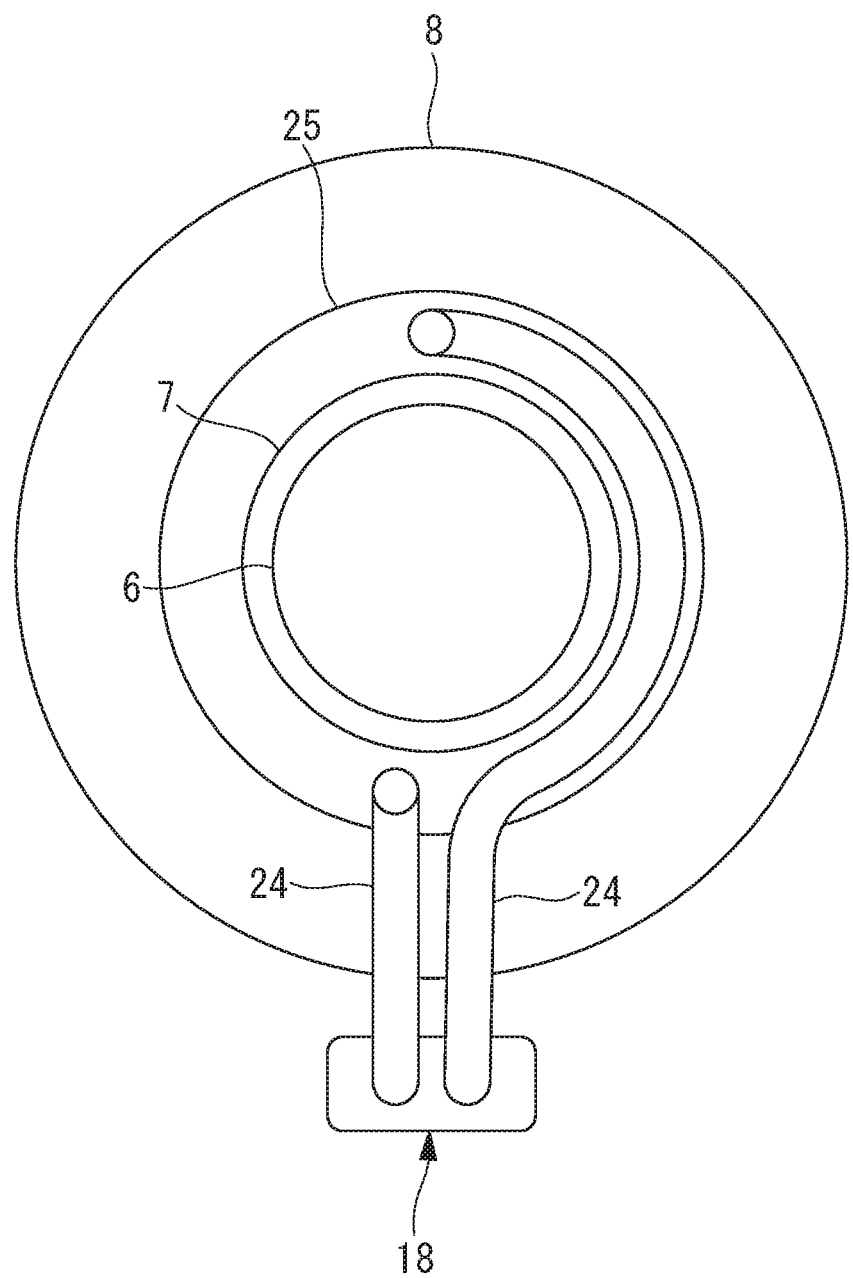
FIG. 11 is a front view illustrating the arrangement of light guide fibers in a modification of the endoscope in FIG. 1.
Figure 12:
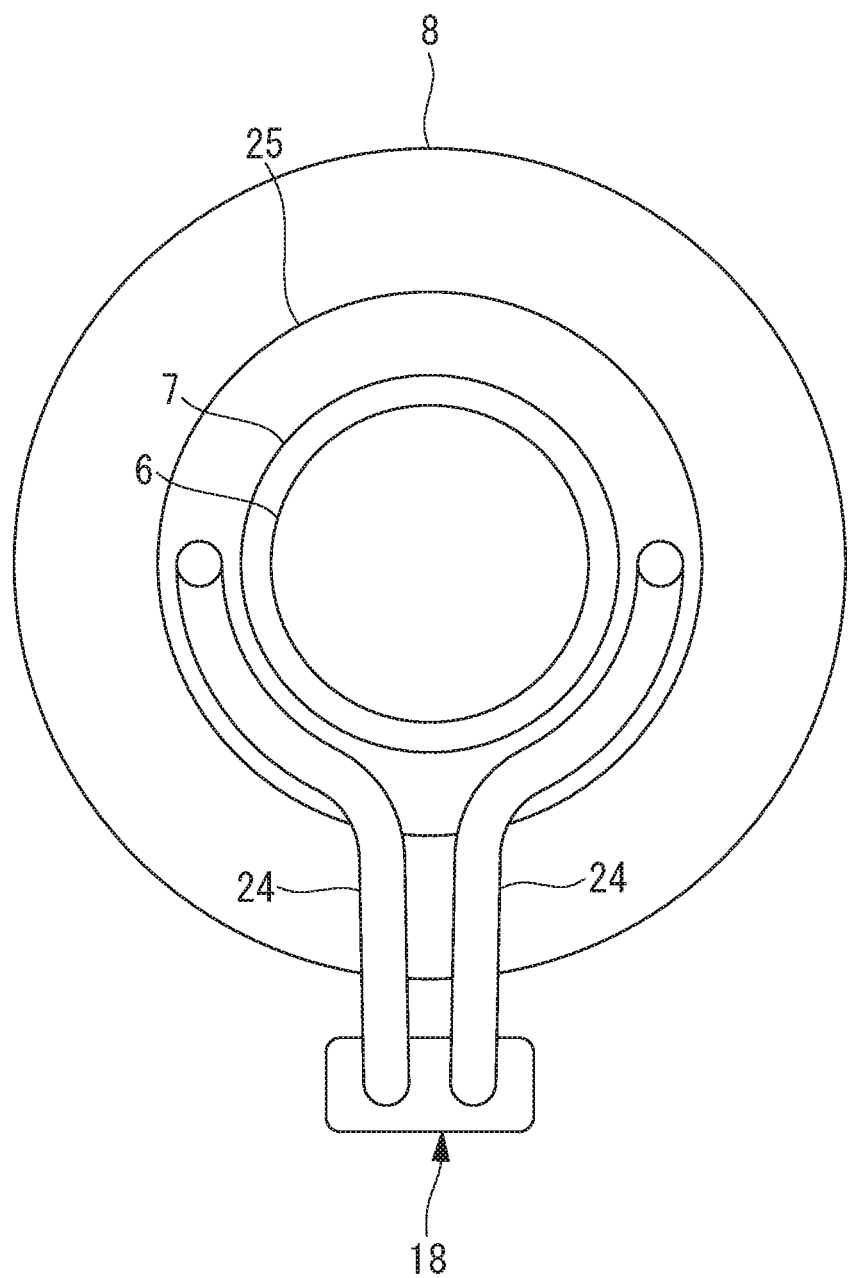
FIG. 12 is a front view illustrating the arrangement of light guide fibers in another modification of the endoscope in FIG. 1.

This embodiment is directed to an example where the three light guide fibers 24 cause the illumination light to enter the three locations arranged at equal intervals in the circumferential direction of the scattering element 25, but is not limited to this example. Two light guide fibers 24 or four or more light guide fibers 24 may be used so that the illumination light is caused to enter two locations or four or more locations. If two light guide fibers 24 are used, the light guide fibers 24 may be disposed so as to cause the illumination light to enter locations separated from each other by 180°, as shown in FIGS. 11 and 12.

As an alternative to this embodiment in which the scattering element 25 has the shape of a ring along the entire circumference, the scattering element 25 may be partially cut off in the circumferential direction or may be split in the circumferential direction.

Figure 13:
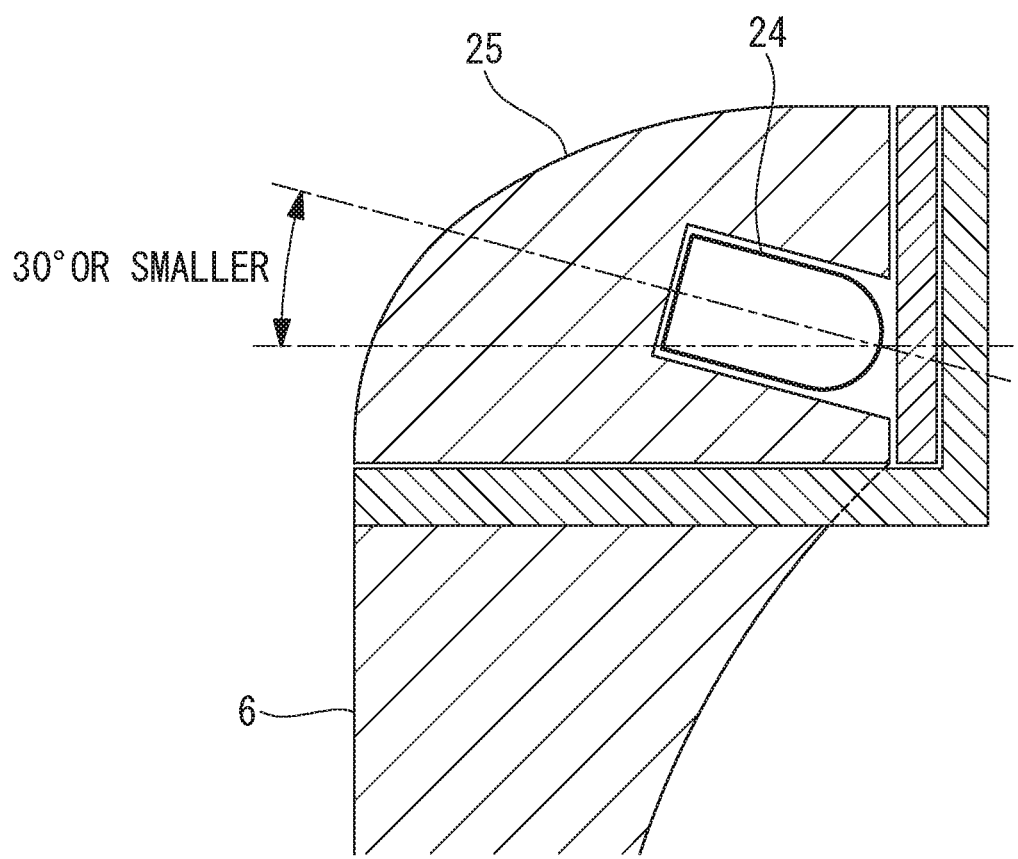
FIG. 13 is a vertical sectional view similar to FIG. 10, in accordance with another modification of the endoscope in FIG. 1.

In this embodiment, the distal end surfaces of the light guide fibers 24 are disposed substantially parallel to the distal end surface of the forward-observation objective lens 6. Alternatively, as shown in FIG. 13, the central axis at the distal end surface of each light guide fiber 24 may be inclined radially outward relative to the optical axis of the forward-observation objective lens 6 from the proximal end toward the distal end.

As mentioned above, the peripheral edge of the scattering element 25 serving as the peripheral edge of the most distal end surface of the insertion section 2 is constituted by a rounded surface, so that when the illumination light is input parallel to the optical axis of the forward-observation objective lens 6, the illumination light may be focused in a direction toward the optical axis due to refraction at the rounded surface, sometimes causing only the central area to be illuminated with high intensity. Thus, by causing the illumination light to be input in the direction in which the central axis is inclined radially outward toward the distal end, uniform illumination is possible such that the central area alone is prevented from being illuminated with high intensity even if refraction occurs at the peripheral edge of the scattering element 25.

Although a common scattering coefficient and a common anisotropy parameter are used in the description of this embodiment, a simple description will be provided below for confirmation (Reference Document: "Absorption and Scattering of Light by Small Particles", Craig F. Bohren, Donald R. Huffman, Wiley-VCH Verlag GmbH & Co. KGaA).

The scattering coefficient $\mu s$ of the scattering element 25 can be expressed using expression (3) indicated below, assuming that the scattering cross section of each particle is defined as $\sigma_a$ and the number density of the particles dispersed in the scattering element 25 is defined as $\rho_s$.

$$\mu s = \rho_s \sigma_s \quad (3)$$

In this case, $\sigma_s$ in expression (3) can be expressed using expression (4) indicated below, assuming that the geometric cross section of each particle is defined as A and the scattering efficiency of the particles is defined as $Q_s$.

$$\sigma_s = Q_s A \quad (4)$$

In this case, $Q_s$ in expression (4) can be expressed using expression (5) indicated below.

{Numerical Expression 1}

$$Q_S = \frac{2}{x^2} \sum_{k=1}^{\infty} (2k+1)(|a_k|^2 + |b_k|^2) \quad (1)$$

where

{Numerical Expression 2}

$$a_k = \frac{n^2 j_k(nx)[xj_k(x)]' - j_k(x)[kxj_x(nx)]'}{n^2 j_k(nx)[xh_k^{(1)}(x)]' - h_k^{(1)}(x)[nxj_k(nx)]'} \quad (2)$$

{Numerical Expression 3}

$$b_k = \frac{j_k(nx)[xj_k(x)]' - j_k(x)[nxj_x(nx)]'}{j_k(nx)[xh_k^{(1)}(x)]' - h_k^{(1)}(x)[nxj_k(nx)]'} \quad (3)$$

{Numerical Expression 4}

$$h_k^{(1)}(z) = j_k(z) + iy_k(z) \quad (4)$$

{Numerical Expression 5}

$$j_k(z) = \sqrt{\frac{\pi}{2z}} J_{k+0.5}(z) \quad (5)$$

{Numerical Expression 6}

$$y_k(z) = \sqrt{\frac{\pi}{2z}} Y_{k+0.5}(z) \quad (6)$$

$J_k+0.5(z)$ in expression (5) and $Y_k+0.5(z)$ in expression (6) are a Bessel function of the first kind and a Bessel function of the second kind, respectively, and i indicates an imaginary unit.

n indicates the ratio of refractive indices of the particles and the transparent resin and is expressed by using expression (7) indicated below.

{Numerical Expression 7}

$$n = \frac{n_2}{n_1} \quad (7)$$

In this case, x indicates the ratio of the radius a of each particle to the wavelength λ of the illumination light and is expressed by using expression (8) indicated below.

{Numerical Expression 8}

$$x = 2\pi \frac{a}{\lambda} \quad (8)$$

The anisotropy parameter g of each particle indicates an average of the cosine of the scattering angle when light is scattered by a single particle and may be a value in the range of $-1 \leq g \leq 1$. In particular, when g=−1, light is scattered only in the direction directly opposite to the incident angle. When g=1, light is scattered only in the same direction as the incident angle (i.e., light is not scattered). When g=0, complete isotropic scattering occurs. The anisotropy parameter g is calculated using expression (9) indicated below.

{Numerical Expression 9}

$$Q_S \cdot g = \frac{4}{x^2} \left[ \sum_{k=1}^{\infty} \frac{k(k+2)}{k+1} \text{Re}\{a_k a_{k+1}^* + b_k b_{k+1}^*\} + \sum_{k=1}^{\infty} \frac{2k+1}{k(k+1)} \text{Re}\{a_k b_k^*\} \right] \quad (9)$$

In expression (9), * indicates a complex conjugate, and Re indicates a real part within the parentheses { }.

An aspect of the present invention provides an endoscope including: an insertion section having narrow shape; a forward observation window and a forward illumination system that are disposed at a distal end surface of the insertion section; a lateral observation window and a lateral illumination system that are disposed toward a proximal end relative to the distal end surface; and an image capturing element that captures an image of light entering via the forward observation window and the lateral observation window. The forward illumination system includes a ring-shaped scattering element disposed at a position surrounding the forward observation window, and a plurality of light guide fibers that cause illumination light guided from a light source to enter, toward a distal end, a plurality of input locations arranged at intervals in a circumferential direction at a proximal end of the scattering element. The scattering element is constituted by dispersing one or more kinds of particles in a homogenous medium composed of a material different from the particles, and satisfies conditional expressions indicated below:

$0.06 \leq \mu s \leq 100$ $0.7 \leq g < 1$ where μs indicates a scattering coefficient (1/mm) of the scattering element and g indicates an anisotropy parameter of the particles.

According to this aspect, the light output from the forward illumination system and the lateral illumination system and reflected by a subject enters the insertion section via the forward observation window and the lateral observation window, and the image of the light is captured by the image capturing element, so that the subject disposed in front of and lateral to the insertion section can be observed.

In the forward illumination system, the illumination light guided by the light guide fibers from the light source enters the proximal end of the scattering element so as to be scattered by and output from the scattering element, thereby mainly illuminating the subject disposed in front of the insertion section. When the scattering coefficient and the anisotropy parameter of the particles satisfy the conditional expressions, the scattering element has relatively low scattering properties, and the illumination light is output without being uniformly scattered.

Because the illumination light is output without being uniformly scattered by the ring-shaped scattering element, the entire scattering element does not emit light with uniform intensity in a ring-shaped manner. Instead, the scattering element emits light with maximum intensity at the input locations of the illumination light from the light guide fibers and emits light with lower intensity in the remaining areas. As a result, the entire scattering element is prevented from becoming a secondary light source, and a ring-shaped patch of light of a scattering member can be prevented from being formed in the image even when the subject to be observed is moist biological tissue. The scattering properties of the scattering element are minimized, so that the amount of light that is not output outside due to internal reflection at the surface thereof and the amount of light returned by back-scattering can be reduced, thereby achieving improved light utilization efficiency.

In the above aspect, the plurality of light guide fibers may be disposed such that proximal end surfaces thereof that receive the illumination light from the light source are grouped together and are disposed at positions facing a light emitting section of the light source.

Accordingly, since the input ends of the plurality of light guide fibers face the light emitting section that outputs the illumination light from the light source, the cost can be reduced owing to the reduced number of light emitting sections, and the insertion section can be reduced in size.

In the above aspect, the light emitting section may be an output end of an optical fiber bundle that optically guides light from the light source in a longitudinal direction of the insertion section.

Accordingly, with the optical fiber bundle, the illumination light from the light source can be optically guided to the vicinity of the distal end of the insertion section in accordance with a space-saving configuration.

In the above aspect, the lateral observation window may be provided in a range between 200° and 300° inclusive in the circumferential direction, and the light guide fibers may be disposed to longitudinally extend across a position of the lateral observation window at a circumferential position where the lateral observation window is not provided.

Accordingly, the illumination light can be optically guided by the light guide fibers by passing through a position where they do not block the visual field of the lateral observation window.

In the above aspect, the light guide fibers may include three or four light guide fibers and may cause the illumination light to enter the input locations arranged at substantially equal intervals in the circumferential direction.

Accordingly, the illumination light for the observation via the forward observation window can be uniformly radiated onto the subject while preventing a ring-shaped patch of light from being formed in the image.

In the above aspect, the light guide fibers may be plastic multicore fibers.

Accordingly, the light guide fibers can be disposed with a small curvature radius in a small, limited space near the distal end of the insertion section.

In the above aspect, a central axis at a distal end of each light guide fiber may be disposed radially outward of the scattering element at an angle ranging between 0° and 30° inclusive relative to an axis orthogonal to the forward observation window from the proximal end toward the distal end.

Accordingly, the illumination light is output from the distal ends of the light guide fibers in a direction in which the illumination light expands in the radial direction of the scattering element toward the distal end. Although the outer periphery of the distal end of the ring-shaped scattering element disposed at the distal end surface of the insertion section is provided with a rounded surface for improving the insertability of the insertion section, even if the illumination light output from the scattering element is refracted by the rounded surface due to this configuration, the illumination light is prevented from being concentrated only in the center, so that a state where the center alone is illuminated with bright light is prevented, whereby uniform illumination can be achieved.

REFERENCE SIGNS LIST 1 endoscope
2 insertion section
6 forward-observation objective lens (forward observation window)
7 forward illumination system
8 lateral-observation objective lens (lateral observation window)
9 illumination lens (lateral illumination system)
10a distal end surface
16 image capturing element
18 light guide (optical fiber bundle)
21 light source device (light source)
24 (multicore fiber) light guide fiber
25 scattering element

The invention claimed is:

1. An endoscope comprising:
an insertion section;
a forward observation window and a forward illumination system disposed at a distal end surface of the insertion section; and
a lateral observation window and a lateral illumination system disposed at a position of the insertion section that is more toward a proximal end of the insertion section relative to the distal end surface,
wherein the forward illumination system includes:
a scattering element disposed at a position surrounding the forward observation window, the scattering element having a ring shape; and
a plurality of light guide fibers that cause illumination light guided from a light source toward a distal end of the insertion section to enter a plurality of input locations provided at a proximal end of the scattering element, the input locations being arranged at intervals in a circumferential direction, and
wherein the scattering element is constituted by dispersing at least one kind of particles in a homogenous medium composed of a material different from the particles, and satisfies conditional expressions indicated below:

$0.06 \leq \mu s \leq 100$ $0.7 \leq g < 1$ wherein μs indicates a scattering coefficient (1/mm) of the scattering element and g indicates an anisotropy parameter of the particles.

2. The endoscope according to claim 1, wherein the light guide fibers are disposed such that proximal end surfaces thereof that receive the illumination light from the light source are grouped together and are disposed at positions facing a light emitting section of the light source.

3. The endoscope according to claim 2, wherein the light emitting section comprises an output end of an optical fiber bundle that optically guides light from the light source in a longitudinal direction of the insertion section.

4. The endoscope according to claim 2, wherein the lateral observation window is provided in a range between 200° and 300° inclusive in the circumferential direction, and
wherein the light guide fibers are disposed to extend across a position of the lateral observation window in a longitudinal direction of the insertion section at a circumferential position of the insertion section where the lateral observation window is not provided.

5. The endoscope according to claim 1, wherein the light guide fibers include three or four light guide fibers and cause the illumination light to enter the input locations which are arranged at substantially equal intervals in the circumferential direction.

6. The endoscope according to claim 1, wherein the light guide fibers comprise plastic multicore fibers.

7. The endoscope according to claim 1, wherein a central axis at a distal end of each light guide fiber is disposed radially outward of the scattering element at an angle ranging between 0° and 30° inclusive relative to an axis orthogonal to the forward observation window from the proximal end toward the distal end.

* * * * *